(12) United States Patent
Lortz et al.

(10) Patent No.: US 7,470,423 B2
(45) Date of Patent: *Dec. 30, 2008

(54) AQUEOUS DISPERSION CONTAINING PYROGENICALLY PREPARED METAL OXIDE PARTICLES AND DISPERSANTS

(75) Inventors: Wolfgang Lortz, Wächtersbach (DE); Christoph Batz-Sohn, Hanau (DE); Steffen Hasenzahl, Hanau (DE); Gabriele Perlet, Großkrotzenburg (DE); Werner Will, Gelnhausen (DE); Ralf Mathiak, Gladbeck (DE); Klaus Jenni, Essen (DE)

(73) Assignees: Degussa AG, Duesseldorf (DE); Goldschmidt AG, Essen (DE)

( * ) Notice: Subject to any disclaimer, the term of this patent is extended or adjusted under 35 U.S.C. 154(b) by 582 days.

This patent is subject to a terminal disclaimer.

(21) Appl. No.: 10/512,684

(22) PCT Filed: May 14, 2003

(86) PCT No.: PCT/EP03/05034

§ 371 (c)(1),
(2), (4) Date: Oct. 27, 2004

(87) PCT Pub. No.: WO03/103816

PCT Pub. Date: Dec. 18, 2003

(65) Prior Publication Data

US 2005/0224749 A1    Oct. 13, 2005

(30) Foreign Application Priority Data

Jun. 6, 2002   (DE) .................. 102 25 125

(51) Int. Cl.
*A61K 8/19* (2006.01)
*A61K 9/10* (2006.01)
*A61K 9/14* (2006.01)

(52) U.S. Cl. .................. 424/59; 424/489; 424/641
(58) Field of Classification Search ............ 252/182.11
See application file for complete search history.

(56) References Cited

U.S. PATENT DOCUMENTS

| 4,471,100 A * | 9/1984 | Tsubakimoto et al. ...... 525/367 |
| 4,589,995 A | 5/1986 | Itoi et al. |
| 5,231,067 A * | 7/1993 | Deller et al. ................. 502/350 |
| 5,553,630 A * | 9/1996 | Dupuis et al. ............... 132/202 |
| 5,788,952 A * | 8/1998 | Gers-Barlag et al. .......... 424/59 |
| 5,817,298 A * | 10/1998 | Galley et al. .................. 424/59 |
| 5,967,964 A * | 10/1999 | Hattori et al. ................. 516/81 |
| 6,066,753 A * | 5/2000 | Turowski-Wanke et al. . 558/208 |
| 6,159,390 A | 12/2000 | Ravet et al. |
| 6,808,769 B2 * | 10/2004 | Batz-Sohn et al. ....... 428/32.37 |
| 2002/0022007 A1 * | 2/2002 | Gers-Barlag et al. .......... 424/59 |
| 2004/0034144 A1 * | 2/2004 | Scharfe et al. ............... 524/442 |
| 2005/0169861 A1 * | 8/2005 | Lortz et al. ................... 424/63 |
| 2006/0104881 A1 * | 5/2006 | Lortz et al. .................. 423/335 |

FOREIGN PATENT DOCUMENTS

| DE | 17 92 798 | 8/1977 |
| EP | 0 216 516 | 4/1987 |
| EP | 0 768 277 | 4/1997 |
| EP | 0 876 841 | 11/1998 |
| EP | 1 070 739 | 1/2001 |
| EP | 1 209 191 | 5/2002 |
| GB | 1 169 352 | 11/1969 |
| JP | 11-19497 | 1/1999 |
| WO | WO 9011067 A1 * | 10/1990 |

* cited by examiner

*Primary Examiner*—Mark Eashoo
*Assistant Examiner*—Peter F Godenschwager
(74) *Attorney, Agent, or Firm*—Oblon, Spivak, McClelland, Maier & Neustadt, P.C.

(57) ABSTRACT

An aqueous dispersion containing pyrogenically prepared oxide particles of titanium, zinc, iron or cerium with an average particle size, expressed as the median, in the dispersion of less than 250 nm, that the particle sizes of the oxide particles in the dispersion are not distributed symmetrically and the dispersion contains, as a dispersant, at least one compound of the formula (I) and/or a maleic anhydride/acrylate copolymer of the general formula (IIa) and/or a maleate/acrylate copolymer of the general formula (IIb). It is prepared by dispersing a predispersion stream by means of a high energy mill. It can be used in sunscreen formulations.

24 Claims, No Drawings

AQUEOUS DISPERSION CONTAINING PYROGENICALLY PREPARED METAL OXIDE PARTICLES AND DISPERSANTS

CROSS REFERENCES TO RELATED APPLICATIONS

This application is a national stage application of International Patent Application No. PCT/EP03/05034, filed on May 14, 2003, and claims priority to German Patent Application No. 102 25 125.8, filed on Jun. 6, 2002, both of which are incorporated herein by reference in their entireties.

The invention provides an aqueous dispersion containing pyrogenically prepared metal oxide particles and a phosphate and/or maleate anhydride/maleate-acrylate copolymer as dispersant, a process for preparing this dispersion and its use to prepare cosmetic formulations, in particular sunscreen formulations.

To protect the skin from too intense UV radiation, cosmetic preparations which contain UV filters, such as cremes or lotions, are used, these being largely transparent on the skin and pleasant to apply.

As UV filters, they contain one or more organic compounds which absorb in the wavelength region between 290 and 400 nm: UVB radiation (290 to 320 nm); UVA radiation (320 to 400 nm).

Energy-rich UVB radiation causes the typical symptoms of sunburn and is also responsible for suppressing the immune defence system, while UVA radiation, which penetrates further into the layers of skin, causes premature ageing of the skin. Since the combined effects of the two types of radiation can encourage the production of skin diseases caused by light, such as skin cancer, the search for possibilities to improve the degree of UV protection already produced even more significantly therefore started at an early stage.

It was found that ultrafine pigments based on metal oxides can also scatter, reflect and absorb UV radiation. Therefore highly disperse formulations of these are an effective supplement to the organic UV filter in suncreens.

Thus, ultrafine titanium dioxide is used in many different ways in cosmetic formulations because it is chemically inert and toxicologically acceptable and does not lead to either skin irritations or to sensitisation. Currently, it is the most frequently used and most important mineral light-protective substance. In addition to titanium dioxide, ultrafine zinc oxide is being used to an increasing extent.

Coarsely divided materials (pigments) and finely divided materials (micropigments) should be differentiated. In the case of micropigments, the average primary particle size is generally well below 200 nm, mostly in the range 10 to 100 nm, generally below 50 nm.

The primary particles are the smallest particles which are produced during preparation of the pigments. Primary particles may be present in the form of individual crystallites or else in the form of several crystallites which have densely intergrown with each other via faces. Aggregates are particles which consist of several primary particles, wherein the primary particles have intergrown with each other in a two-dimensional array. An agglomerate is understood to be an association of primary particles or aggregates which are held together by attractive forces such as, for example, hydrogen bridge bonds.

Coarsely divided pigments (0.2 to 0.5 μm) absorb and/or reflect broadly and relatively evenly over the entire UV region and the region of visible light, whereas finely divided material exhibits a clear increase in effect in the UV region with a simultaneous loss of effect in the longwave UVA and in particular in the visible region. Since only very little of the visible light is reflected, preparations based on these active substances are therefore largely transparent.

A reduction in photochemical activity can be produced by inorganic and organic surface components such as, for example, $Al_2O_3$, $SiO_2$ and/or fatty acid (salts), siloxanes. These substances can adhere to the surface as a result of chemical or physical sorption (lattice doping/coating).

In transparent cosmetic formulations, it is important that the particles are as small as possible so that they cannot be detected on the skin with the naked eye. At the same time, the UV protective effect of a sunscreen should not be reduced and the particles should not settle out during storage.

For this purpose, the aggregated and agglomerated metal oxide particles are dispersed. This process is understood to include the incorporation, reduction in size and uniform distribution of solids in a liquid phase.

In practice, it has been shown that dispersion problems increase with increasing degree of fineness of the particles so that the dispersion process overall is one of the most costly sub-steps in the production of cosmetic formulations. The challenge in practice, therefore, is to separate out the most costly part of the dispersing process, breaking down the agglomerates, from production of the actual cosmetic formulations and to provide stable aqueous dispersions with the highest possible concentration of ultrafine metal oxide particles, these preferably being of low viscosity or at least still pumpable or capable of flowing.

An essential feature of a dispersion is the size of the dispersed particles in the dispersion. This size is called the secondary particle size and describes primary particles, aggregates and agglomerates in the state that they are present in the dispersion. In contrast to data relating only to the primary particle size, information about the secondary particle size reflects the actual situation in the dispersion and in sunscreen formulations.

It is possible to break down the agglomerates and wet the newly created surfaces with the aid of dispersing devices such as dissolvers, ball mills and rotor-stator machines, wherein breaking down depends on the energy introduced. The energy of these dispersing devices is not sufficient for the very fine secondary particle sizes required for cosmetic and sunscreen formulations.

Although dispersing devices with higher energy inputs are known, such as high-energy mills, the disadvantage of these devices is the risk of loosening the external layer in the case of coated particles. On the other hand, it is feared that organic dispersants, which are added to stabilise the dispersion, might be thermally decomposed by the energy input and thus adversely modify the properties of the dispersion.

EP-A-876 841 describes the preparation of a titanium dioxide dispersion using a high energy mill, wherein the average particle size in the dispersion is 0.16 μm. The dispersion is stabilised by adding acetic acid. Due to the odour, this type of stabilisation is unsuitable for cosmetic applications. On the other hand, the stability expected in the region relevant to cosmetic applications, pH about 4.5 to 7.5, is regarded as low because it is in the vicinity of the isoelectric point for titanium dioxide. Although $TiO_2$ particles with sizes of this order of magnitude scatter UV radiation very well, the small size of the particles also leads to an undesired rise in photocatalytic activity.

Thus, the object of the present invention was to prepare a highly concentrated aqueous dispersion of ultrafine metal oxide particles with a comparatively low viscosity which is stable in the physiologically acceptable pH range of 4.5 to 7.5 and which has reduced photocatalytic activity as compared with that of the prior art.

The object is achieved by an aqueous dispersion containing pyrogenically prepared oxide particles of titanium, zinc, iron or cerium with an average particle size, expressed as the median, in the dispersion of less than 250 nm, characterised in that the particle sizes of the oxide particles in the dispersion are not distributed symmetrically and the dispersion contains, as a dispersant, at least one compound of the general formula I

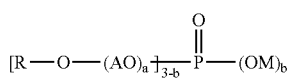

in which
R represents an optionally branched, optionally multiple bond- and optionally hydroxyl group-containing alkyl group with 6 to 22 carbon atoms,
A represents an ethylene group, propylene group, iso-propylene group or butylene group,
M represents H, an alkali metal or an ammonium ion,
a is 0 to 30,
b is 0 to 2 and/or at least one copolymer of the general formula IIa

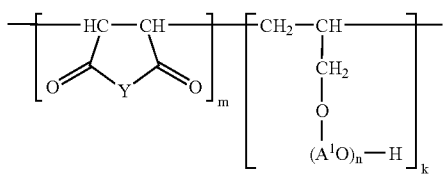

and/or at least one copolymer of the general formula IIb

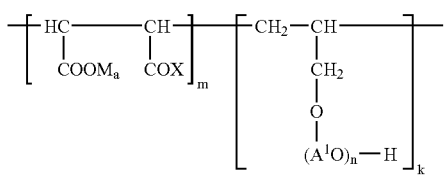

in which, for IIa and IIb
M represents hydrogen, a monovalent or divalent metal cation, an ammonium ion or an organic amine group,
a is 1 or, in the event that M is a divalent metal cation, a=0.5
X represents either $-OM_a$ or $-O-(C_pH_{2p}O)_q-R^1$, where $R^1$=H, or an aliphatic hydrocarbon group with 1 to 20 carbon atoms,
  a cycloaliphatic hydrocarbon group with 5 to 8 carbon atoms, an optionally substituted aryl group with 6 to 14 carbon atoms,
  p=2 to 4, q =0 to 100,
  $-NHR^2$ and/or $-NR^2_2$, where $R^2=R^1$ or $-CO-NH_2$
Y represents O, $NR^2$
$A^1$ represents an ethylene group, a propylene group, an iso-propylene group or a butylene group, m is 10 to 30,
n is 0 to 50,
k is 10 to 30, wherein the sum
m+k is within the range 20 to 60, preferably 20 to 40.

The wording not symmetric is understood to mean that the arithmetic mean of the distribution is greater than the median.

The mean is understood to be the arithmetic mean of the volume-weighted particle size distribution. The median is understood to be the $d_{50}$ value of the volume-weighted particle size distribution.

The asymmetric distribution of the particle sizes in the dispersion according to the invention is surprising. When dispersing pyrogenic, aggregated metal oxide particles, a symmetric normal distribution would be expected to be present, this being recognised when the ratio of the mean and the median values of distribution is 1.

Asymmetric distributions are understood to be, in addition to "skewed" monomodal distributions, also multimodal distributions.

Thus, for example, the dispersion of pyrogenically prepared aluminium oxide using high dispersion energies leads to a symmetric normal distribution. The asymmetric distribution of the dispersion according to the invention means that a large proportion of the particles has the fineness desired for cosmetic applications, whereas a smaller proportion of coarser particles has a beneficial effect on the stability and rheology of the dispersion.

Pyrogenically prepared oxide particles of titanium, zinc, iron and cerium include those which arise from flame hydrolysis and also those which arise from a flame oxidation process. In the case of flame hydrolysis, precursors of the metal oxides, for example metal halides or organometallic compounds, are burnt in a hydrogen/oxygen flame, wherein the precursors are hydrolysed. This synthetic method, originally described for pyrogenic silicon dioxide, can also be used, for example, for titanium dioxide. In the case of flame oxidation, metal vapour is generally oxidised to the metal oxide in an atmosphere of oxygen. The oxidation of zinc vapour to zinc oxide may be mentioned by way of example. From a toxicological and dermatological point of view, harmless compounds such as cerium oxide, zinc oxide, iron oxide and in particular titanium dioxide are suitable for cosmetic formulations. Furthermore, the oxide particles also include mixed oxide particles, doped particles or coated particles of titanium, zinc, iron and cerium with each other and/or with silicon and/or aluminium. The BET surface area of the oxide particles may vary over a wide range, from 5 to 200 $m^2$/g.

The surfaces of the previously mentioned metal oxide particles may also be further modified with organic compounds. Water-repellent metal oxide particles can be obtained in this way. Examples of metal oxide particles modified with organic compounds are described, for example, in DE-A-42 02 695, EP-A-1 078 957, EP-A-924 269, EP-A-722 992.

The metal oxide particles to be used according to the invention may be, for example, commercially available products which are obtainable under the relevant trade names, also with inorganic or organic coatings, such as for example Micro Titanium Dioxide MT 100 AQ and MT 150 W (Tri-K-Tayca), UV-Titan M 212 (Kemira), and titanium dioxide P-25 (Degussa).

Titanium dioxide T 805 (Degussa) has proven especially advantageous here. Titanium dioxide T 805 consists, crystallographically of about 80% anatase and about 20% rutile and is coated with trialkoxyoctylsilane. It is characterised by decreased photoactivity, reduced surface activity, high cosmetic acceptability and very good water-resistance.

The dispersion may contain 20 to 60 wt. %, preferably 30 to 50 wt. %, of metal oxide particles.

The phosphates used according to the invention are represented in idealised form by the general formula (I)

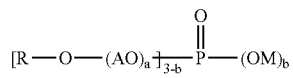

As a result of the industrial method of preparation, mixtures are present in which the desired main components, according to the invention preferably the monoester and diester, are mainly present as well as small proportions of the other possible reaction products.

They are prepared by reacting fatty alcohols R—OH or fatty alcohol alkoxylates R—O-(AO)$_a$—H with phosphoric acid or its derivatives by known processes.

The fatty alcohols being used can be prepared by well-known processes by reducing fatty acids or their esters in the presence of catalysts. In the case of direct hydrogenation, fatty alcohols from triglycerides by reaction with hydrogen on a Cu/Cr catalyst in a one-step process in a tubular reactor, wherein the fatty alcohol, 1,2-propanediol and water are produced as the reaction products. In another process, a fatty alcohol is prepared from triglycerides via a transesterification step followed by hydrogenation of the fatty acid ester.

Fatty acids which may be used, individually or as mixtures, are fatty acids such as n-caprylic acid, capric acid, 2-ethylhexanoic acid, lauric acid, myristic acid, palmitic acid, palmitoleic acid, isostearic acid, stearic acid, hydroxystearic acid (ricinoleic acid), dihydroxystearic acid, oleic acid, linoleic acid, petrolesic acid, elaidic acid, arachidic acid, behenic acid and erucic acid, gadoleic acid and the technical grade mixtures produced during the pressurised cracking of natural fats and oils such as oleic acid, linoleic acid, linolenic acid, and in particular rape-seed oil fatty acid, soy oil fatty acid, sunflower oil fatty acid, tall oil fatty acid. In principle, all fatty acids with similar chain distributions are suitable.

The concentration in these fatty acids or fatty acid esters of unsaturated fractions is, unless this is required, adjusted down to a desired iodine value by the well-known catalytic hydrogenation process or is produced by mixing fully hydrogenated with non-hydrogenated fatty components. The iodine value, as a measure of the average degree of saturation of a fatty acid, is the amount of iodine which is taken up by 100 g of compound in order to saturate the double bonds.

Preferably used are the alcohols from partially cured $C_{8/18}$-coconut or palm oil fatty acids, rape-seed oil fatty acids, sunflower oil fatty acids, soy oil fatty acids and tall oil fatty acids with iodine values in the range about 80 to 150 and in particular the alcohols from technical grade $C_{8/18}$-coconut fatty acids, wherein a choice of cis/trans isomers such as the elaidic acid-rich $C_{16/18}$-fatty acid fraction may optionally be of advantage. They are commercially available products and are offered by a variety of companies under their particular trade names.

In addition to fatty alcohols, in particular guerbet alcohols and their alkoxylates may also be used.

The alcohol alkoxylates R—O-(AO)$_a$—H may be obtained by well-known processes by the addition of alkylene oxides in the presence of acid or basic catalysts.

The -(AO)$_a$— group here represents groups such as ethylene oxide, propylene oxide, butylene oxide and/or tetrahydrofuran, preferably ethylene oxide, wherein a represents an average value of up to 30, preferably 3 to 15 units.

In the general formula -(AO)$_a$— represents either a homopolymer of one of the alkylene oxides mentioned or block copolymers or copolymers with random distribution of two or more of the monomers in the polymer molecule.

In phosphates of the general formula I, R may advantageously be a fatty alcohol group with 6 to 22 carbon atoms, preferably 12 to 18 carbon atoms and a has a value between 1 and 30, preferably 3 to 15.

In phosphates of the general formula I, R may represent a guerbet alcohol group with 6 to 22 carbon atoms, preferably 12 to 18 carbon atoms and a has a value between 1 and 30, preferably 3 to 15.

These products are commercially available. They are used in amounts of 0.5 to 30% with respect to the aqueous dispersion, preferably 3 to 15% with respect to the aqueous dispersion.

In the copolymers of the general formula IIa and IIb being used in accordance with the invention,

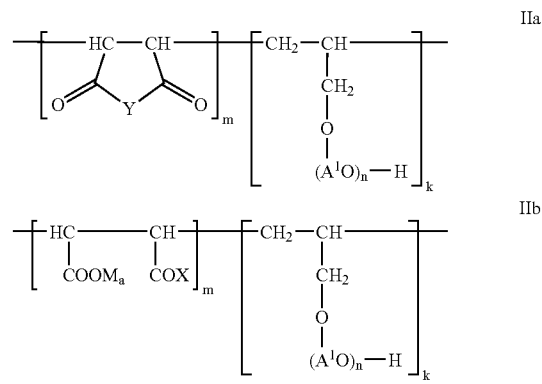

the following definitions apply:

M represents hydrogen, a monovalent or divalent metal cation, an ammonium ion or an organic amine group a is 1 or, in the event that M is a divalent metal cation, a =0.5

X represents either —OM$_a$ or —O—(C$_p$H$_{2p}$O)$_q$—R$^1$ where
  R$^1$=H or an aliphatic hydrocarbon group with 1 to 20 carbon atoms,
  a cycloaliphatic hydrocarbon group with 5 to 8 carbon atoms, an optionally substituted aryl group with 6 to 14 carbon atoms,
  p =2 to 4, q =0 to 100,
  or —NHR$^2$ and/or —NR$^2_2$ where R$^2$=R$^1$ or —CO—NH$_2$ Y represents O, NR$^2$ A$^1$ represents an ethylene group, a propylene group, an isopropylene group or a butylene group, m is 10 to 30, n is 0 to 50, k is 10 to 30, wherein the sum m +k is in the range 20 to 60, preferably 20 to 40, -(A$^1$O)$_n$— represents either a homopolymer of one of the alkylene oxides mentioned or else block copolymers or copolymers with random distribution of two or more of the monomers in the polymer molecule, the units

[ ]$_m$ and [ ]$_k$ may also be present as block copolymers or copolymers with random distribution of two or more of the monomers in the polymer molecule.

Sodium, potassium, calcium or magnesium ions are preferably used as the monovalent or divalent metal cations M.

The organic amine groups used are preferably substituted ammonium groups which are derived from primary, secondary or tertiary $C_1$- to $C_{20}$-alkylamines, $C_1$- to $C_{20}$-alkanolamines, $C_5$- to $C_8$-cycloalkylamines and $C_6$- to $C_{14}$-arylamines. Examples of appropriate amines are methylamine, dimethylamine, trimethylamine, ethanolamine, diethanolamine, triethanolamine, cyclohexylamine, dicyclohexylamine, phenylamine, diphenylamine in the protonated (ammonium) form.

X may represent —$OM_a$ or —$O$—$(C_pH_{2p}O)_q$—$R^1$ where $R^1$=H, an aliphatic hydrocarbon group with 1 to 20 carbon atoms, a cycloaliphatic hydrocarbon group with 5 to 8 carbon atoms, an aryl group with 6 to 14 carbon atoms, which may also optionally be substituted. p may have a value from 2 to 4, q=0 to 100, wherein in a preferred embodiment, p=2 or 3, and is thus derived from polyethylene oxide or polypropylene oxide.

Alternatively, X may also represent —$NHR^2$ and/or —$NR^2_2$ where $R^2$=$R^1$ or —CO—$NH_2$, which corresponds to the mono- or disubstituted monoamide of the corresponding unsaturated carboxylic acid.

Y may be 0 (acid anhydride) or $NR^2$ (acid imide).

A copolymer of the general formula IIa or IIb may preferably be used, wherein $A^1$ is an ethylene group, m is 10 to 30, n is 5 to 20, k is 10 to 30 and wherein the sum m +k is within the range 20 to 40.

Compounds of the general formula IIa or IIb may also preferably be used in which R is an alkyl group with 8 to 18 carbon atoms which is optionally branched, optionally contains multiple bonds, optionally contains hydroxyl groups, and A is an ethylene group, M =H or an alkali metal, a is 1 to 30, b is 1 or 2.

These products may contain compounds of the general formula IIa or IIb in amounts of 0.5 to 30 wt. %, preferably 1 to 15 wt. % or, in total, 0.5 to 30 wt. %, preferably 1 to 15 wt. %, of compounds of the general formula IIa and IIb.

In addition to the components mentioned, further additives and auxiliary substances which are known in this field may also be used, if required, such as ethanol, propanol, butanol, propylene glycol, butylene glycol, pentylene glycol, hexylene glycol, alkoxylates, glycol ethers, glycols, polyethylene glycols, polypropylene glycols, Polybutylene glycols, glycerine esterethoxylates, glycerine, polyglycerine, sorbitol, sucrose, fructose, galactose, mannose, polysorbates, starch, xanthan gum, carrageenan gum, cellulose derivatives, alginates, glycol esters, sorbitane esters, opacifiers, solubilisers, ethoxylated fatty alcohols, sodium chloride, sodium sulfate, magnesium sulfate, buffer systems, cholesterol, pantothenic acid, ascorbic acid, polyacrylic acids, carbomers.

The dispersion according to the invention may have a zeta potential of less than −20 mV in the pH range 4.5 to 7.5. The zeta potential is the outwardly effective potential of the particles and is a measure of the electrostatic interaction between individual particles. It plays a part in stabilising suspensions and in particular dispersions with dispersed ultrafine particles. When there is a zeta potential of <−20 mV or >+20 mV there is a strong repulsion between the particles and the dispersions remain stable. With values within this range, the repulsion is so low that the van-der-waals forces enable the formation of agglomerates and this leads to undesired sedimentation of the particles.

A zeta potential of less than −20 mV, however, is only one embodiment of the invention. The stability of the dispersion according to the invention is not determined only by an electrostatic interaction. Example 3 describes a stable dispersion (Table 4) with a zeta potential of only −2.8 mV.

The dispersion according to the invention may also have a viscosity of less than 2000 mPas at a rate of shear of 100 s$^{-1}$.

The invention also provides a process for preparing the dispersion which is characterised in that a stream of a predispersion which contains pyrogenically prepared metal oxide particles, each time at least one compound of the general formula I and/or at least a copolymer of the general formula IIa and/or at least a copolymer of the general formula IIb, water and optionally additional auxiliary substances, is divided into at least two sub-streams, these sub-streams are subjected to a pressure of at least 500 bar, preferably 500 to 1500 bar, particularly preferably 2000 to 3000 bar, in a high energy mill, returned to atmospheric pressure via a nozzle and collide with each other and are milled in a gas or liquid filled reaction chamber.

High energy mills are commercially available devices. Suitable devices for preparing the dispersion according to the invention are, for example, an Ultimaizer, from the Sugino Co., or the one described in DE-A-100 37 301.

Predispersion can be achieved, for example, using dissolvers, rotor-stator machines or ball mills. The use of rotor-stator machines is preferred.

The dispersion stream can be circulated in a system so that the dispersion is milled several times using a high energy mill.

Dispersions according to the invention are preferably used to produce cosmetic formulations such as make-up, coloured powder, lipsticks, hair dyes, day cremes and in particular sunscreen preparations and may be presented in conventional forms such as, for example, water-in-oil or oil-in-water dispersions (emulsions), gels, cremes, lotions, sprays.

The dispersions obtained are characterised by the high degree of fineness of the dispersed solids, long-term storage stability, low viscosity and high photostability.

EXAMPLES

The constituents of the dispersion listed in Table 1, apart from the TiO$_2$ particles, are initially introduced (batch size about 75 kg). Then the particles are drawn in through the suction tube of the Ystral Conti-TDS 3 under shear conditions and the shear process is continued at 3000 rpm for a further 15 min after the end of this procedure (sample 0, see Table 2). This predispersion is passed, up to five times, through the high energy Sugino Ultimaizer HJP-25050 mill at a pressure of 2500 bar with diamond nozzles of 0.3 mm diameter and a sample is taken after each passage through the mill (1st passage is sample 1, 2nd passage is sample 2 etc.; see Table 2). Table 3 gives the viscosities and Table 4 gives the zeta potentials of selected examples.

TABLE 1

| | Formulations (in wt. %) | | | | |
|---|---|---|---|---|---|
| Example | 1 | 2 | 3 | 4 | 5 |
| TiO$_2$ particles | 40 | 33 | 35 | 40 | 40 |
| Rewophat EAK 8190 a compound of the formula I | 2 | 2 | — | 5 | — |
| Guerbet alcohol C$_{12}$ EO-4-phosphate, a compound of the formula I, b = 1 to 2; M = H | — | — | — | — | 6 |
| Compound of the formula IIb (MW 15,000) | — | — | 21 | 14 | 16 |
| Glycerine | — | — | 10 | 10 | 10 |

TABLE 1-continued

| | Formulations (in wt. %) | | | | |
|---|---|---|---|---|---|
| Example | 1 | 2 | 3 | 4 | 5 |
| Fully deionised water | 58.0 | 65 | 34 | 31 | 28 |

Examples 1 and 3 (Degussa AG): P25; example 2: TN90 (Nippon Aerosil), Examples 4 and 5: T 805 (Degussa AG)

TABLE 2

Particle size distribution [in nm][1)]

| | | Example | | | | |
|---|---|---|---|---|---|---|
| Sample | | 1 | 2 | 3 | 4 | 5 |
| 0 | Median | 256 | 216 | 310 | 260 | 236 |
| | Mean | 289 | 240 | 335 | 281 | 248 |
| | Mean/Median | 1.13 | 1.11 | 1.08 | 1.08 | 1.05 |
| 1 | Median | 254 | 148 | 281 | 174 | 107 |
| | Mean | 267 | 189 | 318 | 205 | 154 |
| | Mean/Median | 1.05 | 1.28 | 1.13 | 1.18 | 1.44 |
| 2 | Median | n.d. | 105 | 229 | 135 | 97 |
| | Mean | | 140 | 268 | 159 | 137 |
| | Mean/Median | | 1.33 | 1.17 | 1.18 | 1.41 |
| 3 | Median | 154 | n.d. | n.d. | n.d. | n.d. |
| | Mean | 193 | | | | |
| | Mean/Median | 1.25 | | | | |

[1)]determined using the Malvern Zetasizer 3000 HSa instrument applying the principle of dynamic light scattering. The results are obtained from volume-weighted Contin analysis;

TABLE 3

Viscosity of the dispersions [in mPas] as a function of the rate of shear [in s$^{-1}$]

| | Rate of | Example | | | | |
|---|---|---|---|---|---|---|
| Sample | shear | 1 | 2 | 3 | 4 | 5 |
| 0 | 1 | 66700 | 28700 | 2420 | 408 | 34900 |
| | 100 | 188 | 324 | 4595 | 266 | 1400 |
| 2 | 1 | 5790 | 31000 | 359 | 76 | 15700 |
| | 100 | 131 | 439 | 130 | 69 | 518 |

* The viscosity was determined as the change in viscosity using a Physica MCR 300 viscometer and the CC27 measuring system

TABLE 4

Zeta potentials[1)] in mV at selected pHs and isoelectric points (IEP)

| | Example | | | | |
|---|---|---|---|---|---|
| | 1 | 2 | 3 | 4 | 5 |
| mv/pH | −29.7/5.0 | −26.3/5.2 | −2.8/6.5 | −23.4/6.2 | −22.1/6.4 |
| IEP at pH | <2 | <2 | 2.7 | n.p. | n.p. |

[1)]The zeta potential was determined with the DT-1200 instrument from Dispersion Technology Inc., USA.;
n.p. = not present (IEPs could not be found over the entire range from pH 2 to pH 10)

The dispersions according to the invention are storage-stable for more than 6 months at room temperature and for more than 1 month at 50° C.

The invention claimed is:

1. An aqueous dispersion comprising pyrogenically prepared oxide particles of titanium, zinc, iron or cerium with an average particle size, expressed as the median, in the dispersion of less than 250 nm, wherein the particle sizes of the oxide particles in the dispersion are not distributed symmetrically and the dispersion comprises, as a dispersant, at least one compound of the general formula I

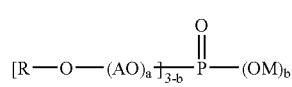

wherein
R represents an optionally branched, optionally multiple bond- and optionally hydroxyl group-comprising alkyl group with 6 to 22 carbon atoms,
A represents an ethylene group, propylene group, iso-propylene group or butylene group,
M represents H, an alkali metal or an ammonium ion,
a is 0 to 30,
b is 0 to 2,
and at least one copolymer of the general formula IIa

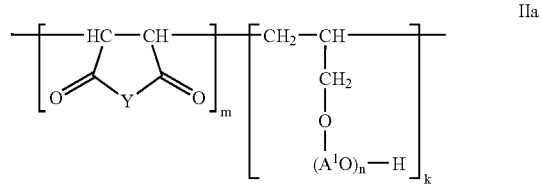

and optionally at least one copolymer of the general formula IIb

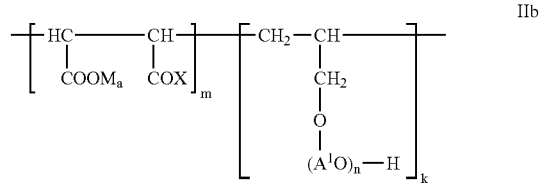

wherein, for IIa and IIb
M represents hydrogen, a monovalent or divalent metal cation, an ammonium ion or an organic amine group,
a is 1 or, in the event that M is a divalent metal cation, a=0.5,
X represents either —OM$_a$ or —O—(C$_p$H$_{2p}$O)$_q$ -R$^1$, where R$^1$ =H, or an aliphatic hydrocarbon group with 1 to 20 carbon atoms,
a cycloaliphatic hydrocarbon group with 5 to 8 carbon atoms,
an optionally substituted aryl group with 6 to 14 carbon atoms,
p =2 to 4, q =0 to 100,
—NHR$^2$ and/or —NR$^2$$_2$, where R$^2$ =R$^1$ or —CO—NH$_2$ Y represents O, NR$^2$ A$^1$ represents an ethylene group, a propylene group, an iso-propylene group or a butylene group, m is 10 to 30, n is 0 to 50, k is 10 to 30, wherein the sum m+k is within the range 20 to 60.

2. The aqueous dispersion according to claim 1, wherein the metal oxide particles comprise the oxides of titanium, zinc, iron, cerium, mixtures thereof and mixed oxides of titanium, zinc, iron, cerium, and mixtures thereof with aluminium or silicon.

3. The aqueous dispersion according to claim 1, wherein the surface of the metal oxide particles has been modified using organic compounds.

4. The aqueous dispersion according to claim 1, wherein said aqueous dispersion comprises 20 to 60 wt.% of metal oxide particles.

5. The aqueous dispersion according to claim 1, wherein in compounds of the general formula I, R represents a fatty alcohol group with 6 to 22 carbon atoms, and a has a value between 1 and 30.

6. The aqueous dispersion according to claim 1, wherein in the phosphate of the general formula I, R represents a guerbet alcohol group with 6 to 22 carbon atoms, and a has a value between 1 and 30.

7. The aqueous dispersion according to claim 1, wherein said aqueous dispersion comprises 0.5 to 30 wt.% of the phosphate of the general formula I.

8. The aqueous dispersion according to claim 1, wherein A$^1$ is an ethylene group, m is 10 to 30, n is 5 to 20, k is 10 to 30 and the sum m +k is within the range 20 to 40, in copolymers of the general formula IIa, and if present, IIb.

9. The aqueous dispersion according to claim 1, wherein R represents an optionally branched alkyl group with 8 to 18 carbon atoms which optionally comprises multiple bonds and optionally comprises hydroxyl groups and A is an ethylene group, M =H or an alkali metal, a is 1 to 30, and b is 1 or 2, in compounds of the general formula I.

10. The aqueous dispersion according to claim 1, wherein said aqueous dispersion comprises 0.5 to 30 wt.% of copolymers of the general formula IIa or in total 0.5 to 30 wt.% of copolymers of the general formula IIa, and if present, IIb.

11. The aqueous dispersion according to claim 1, wherein said aqueous dispersion further comprises auxiliary substances and additives.

12. The aqueous dispersion according to claim 1, wherein said aqueous dispersion has a zeta potential of less than −20 mV in the pH range 4.5 to 7.5.

13. The aqueous dispersion according to claim 1, wherein said aqueous dispersion has a viscosity of less than 2000 mPas at a rate of shear of 100 s$^{-1}$.

14. The aqueous dispersion according to claim 1, wherein said at least one copolymer of the general formula IIb is present.

15. The aqueous dispersion according to claim 1, wherein for IIa and IIb, m+k is within the range of 20 to 40.

16. The aqueous dispersion according to claim 1, wherein in compounds of the general formula I, R represents a fatty alcohol group with 12 to 18 carbon atoms, and a has a value between 3 to 15.

17. The aqueous dispersion according to claim 1, wherein in the phosphate of the general formula I, R represents a guerbet alcohol group with 12 to 18 carbon atoms, and a has a value between 3 and 15.

18. The aqueous dispersion according to claim 1, wherein said aqueous dispersion comprises 3 to 15 wt.% of the phosphate of the general formula I.

19. A process for preparing the dispersion according to claim 1, wherein a stream of a predispersion which comprises pyrogenically prepared metal oxide particles, each time at least one compound of the general formula I and/or at least a copolymer of the general formula IIa and/or if present, at least a copolymer of the general formula IIb, water and optionally additional auxiliary substances, is divided into at least two sub-streams, said at least two sub-streams are subjected to a pressure of at least 500 bar, in a high energy mill, returned to atmospheric pressure via a nozzle and collide with each other and are milled in a gas or liquid filled reaction chamber.

20. The process according to claim 19, wherein the dispersion is milled several times using a high energy mill.

21. The aqueous dispersion according to claim 1, wherein said aqueous dispersion comprises 1 to 15 wt.% of copolymers of the general formula IIa or in total 1 to 15 wt. % of copolymers of the general formula IIa, and if present, IIb.

22. The process according to claim 19, wherein said at least two sub-streams are subjected to a pressure of 500 to 1500 bar.

23. The process according to claim 19, wherein said at least two sub-streams are subjected to a pressure of 2000 to 3000 bar.

24. A method of preparing a cosmetic formulation, said method comprising preparing said cosmetic formulation which comprises said aqueous dispersion as claimed in claim 1.

* * * * *